United States Patent
Mei et al.

(10) Patent No.: US 11,045,255 B2
(45) Date of Patent: *Jun. 29, 2021

(54) OPTIMIZING PATIENT TREATMENT RECOMMENDATIONS USING REINFORCEMENT LEARNING COMBINED WITH RECURRENT NEURAL NETWORK PATIENT STATE SIMULATION

(71) Applicant: International Business Machines Corporation, Armonk, NY (US)

(72) Inventors: Jing Mei, Beijing (CN); Shi Wan Zhao, Beijing (CN); Gang Hu, Beijing (CN); Jing Li, Beijing (CN); Eryu Xia, Beijing (CN); En Liang Xu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 693 days.

This patent is subject to a terminal disclaimer.

(21) Appl. No.: 15/820,237

(22) Filed: Nov. 21, 2017

(65) Prior Publication Data
US 2019/0059998 A1 Feb. 28, 2019

Related U.S. Application Data

(63) Continuation of application No. 15/690,436, filed on Aug. 30, 2017, now Pat. No. 10,881,463.

(51) Int. Cl.
*G16H 50/50* (2018.01)
*G16H 40/20* (2018.01)
(Continued)

(52) U.S. Cl.
CPC ........ *A61B 34/10* (2016.02); *G06F 16/90335* (2019.01); *G06F 19/00* (2013.01);
(Continued)

(58) Field of Classification Search
None
See application file for complete search history.

(56) References Cited

U.S. PATENT DOCUMENTS 9,805,028 B1 * 10/2017 Sutskever ............... G06F 40/20
9,996,670 B2 * 6/2018 Dejori .................... G16H 50/70
(Continued)

OTHER PUBLICATIONS

Wikipedia, "Convergence (logic)", https://en.wikipedia.org/wiki/Convergence_(logic), Last edited on Sep. 25, 2014, Printed on Aug. 28, 2017, 1 page.

(Continued)

*Primary Examiner* — Michael Tomaszewski
*Assistant Examiner* — Jay M. Patel
(74) *Attorney, Agent, or Firm* — Scully, Scott, Murphy & Presser, P.C.; Joseph Petrokaitis

(57) ABSTRACT

Patient treatment may be optimized using Recurrent Neural Network (RNN) based state simulation and Reinforcement learning (RL) techniques to simulate future states and actions. A RNN state simulator and a RL action generator may be trained using patient data such as historical states and actions. The RL action generator may be optimized by applying the RNN state simulator to simulating future states and applying the RL action generator to generate recommended actions based on the simulated future states. This process may be iteratively performed until a computational convergence is reached by the RL action generator which may indicate that the RL action generator has been optimized. A patient state may be fed into the optimized RL action generator to generate an optimal recommended treatment action.

11 Claims, 7 Drawing Sheets

(51) Int. Cl.
*G16H 50/20* (2018.01)
*A61B 34/10* (2016.01)
*G06F 19/00* (2018.01)
*G06N 3/08* (2006.01)
*G06F 16/903* (2019.01)
*G06N 3/04* (2006.01)
*G06N 3/00* (2006.01)

(52) U.S. Cl.
CPC .......... *G06N 3/006* (2013.01); *G06N 3/0445* (2013.01); *G06N 3/08* (2013.01); *G16H 40/20* (2018.01); *G16H 50/20* (2018.01); *G16H 50/50* (2018.01)

(56) References Cited

U.S. PATENT DOCUMENTS

| | | | | |
|---|---|---|---|---|
| 2007/0162410 A1* | 7/2007 | Hinchey | ................ | G06N 5/04 706/48 |
| 2010/0056946 A1* | 3/2010 | Holmes | ................ | A61B 5/01 600/549 |
| 2011/0004588 A1* | 1/2011 | Leitersdorf | ........... | G06F 16/951 707/711 |
| 2011/0288835 A1* | 11/2011 | Hasuo | ................ | G06K 9/6297 703/2 |
| 2012/0016690 A1* | 1/2012 | Ramarajan | ............ | G16H 50/20 705/2 |
| 2015/0019241 A1* | 1/2015 | Bennett | ................ | G16H 50/20 705/2 |
| 2015/0100530 A1* | 4/2015 | Mnih | ................ | G06N 20/00 706/25 |
| 2015/0154721 A1* | 6/2015 | Thompson | ............ | G16H 50/30 705/2 |
| 2015/0193583 A1* | 7/2015 | McNair | ................ | G16H 50/20 705/2 |
| 2015/0227710 A1* | 8/2015 | Pappada | ................ | G16H 70/20 705/2 |
| 2015/0301510 A1* | 10/2015 | Dull | ................ | G05B 13/027 706/23 |
| 2015/0363691 A1* | 12/2015 | Gocek | ................ | G06F 21/445 706/16 |
| 2016/0247079 A1* | 8/2016 | Mewes | ................ | G06N 5/048 |
| 2017/0071671 A1* | 3/2017 | Neumann | ............ | G16H 50/20 |
| 2017/0124269 A1* | 5/2017 | McNair | ................ | G16H 10/60 |
| 2017/0277841 A1* | 9/2017 | Shankar | ................ | G06F 19/00 |
| 2017/0364637 A1* | 12/2017 | Kshepakaran | ......... | G16H 10/60 |
| 2018/0012137 A1* | 1/2018 | Wright | ................ | G05B 15/02 |
| 2018/0144243 A1* | 5/2018 | Hsieh | ................ | G06N 3/0454 |
| 2018/0211010 A1* | 7/2018 | Malhotra | .............. | G16H 50/70 |

OTHER PUBLICATIONS

Wikipedia, "Recurrent neural network", https://en.wikipedia.org/wiki/Recurrent_neural_network, Last edited on Aug. 15, 2017, Printed on Aug. 28, 2017, 10 pages.
Wikipedia, "Long short-term memory", https://en.wikipedia.org/wiki/Long_short-term_memory, Last edited on Aug. 27, 2017, Printed on Aug. 28, 2017, 5 pages.
Wikipedia, "Reinforcement learning", https://en.wikipedia.org/wiki/Reinforcement_learning, Last edited on Jul. 20, 2017, Printed on Aug. 28, 2017, 9 pages.
Wikipedia, "Q-learning", https://en.wikipedia.org/wiki/Q-learning, Last edited on Aug. 8, 2017, Printed on Aug. 28, 2017, 5 pages.
List of IBM Patents or Patent Applications Treated As Related.

* cited by examiner

… (1/2)

OPTIMIZING PATIENT TREATMENT RECOMMENDATIONS USING REINFORCEMENT LEARNING COMBINED WITH RECURRENT NEURAL NETWORK PATIENT STATE SIMULATION

BACKGROUND

The present disclosure generally relates to systems and methods for discovering and recommending treatments for a variety of illness, and more particularly, to automated methods for providing optimal treatment recommendations using reinforcement learning (RL) optimization trained with patient state simulation from a recurrent neural-network (RNN).

There currently is a huge market for Clinical Decision Support Systems (CDSS), and by estimation, the CDSS market is estimated worth to $558 million by 2018. One of the promising applications in CDSS is treatment recommendation, which is a very challenging problem.

Recent methods for treatment recommendation may be roughly divided into two categories, knowledge-based and data-driven. Knowledge-based methods typically implement a computerization of clinical guidelines to provide treatment recommendations. However, such knowledge-based methods often require a large amount of manual effort from domain experts, clinicians, or other policy makers. Data-driven methods typically leverage various machine learning algorithms and attempt to rank different treatments for recommendation.

BRIEF SUMMARY

The system, method, and computer program product described herein leverage previous sequential patient observations to provide a treatment recommendation that takes into account long-term utilities for an optimal treatment recommendation. Reinforcement learning is utilized in conjunction with RNN-based simulations for treatment recommendation allowing the reinforcement learning to gradually reach a final optimal treatment policy after reaching a convergence that meets long term future goals.

In an aspect of the present disclosure, a method implemented by at least one processor including hardware is disclosed. The method includes receiving patient data of a plurality of patients from a patient database, training a Reinforcement Learning (RL) action generator based at least in part on the received patient data of the plurality of patients to generate recommended treatment actions based on at least one state of a patient, training a Recurrent Neural Network (RNN) state simulator based at least in part on the patient data of the plurality of patients to simulate new states of a patient based on recommended treatment actions generated by the RL action generator, applying the RL action generator to a state of a patient in the patient data to determine a next recommended treatment action for the patient, determining whether a convergence in the RL action generator has been reached, and optimizing the RL action generator until the convergence in the RL action generator is determined to be reached by iteratively repeating: applying the RNN state simulator to the determined next recommended treatment action to simulate a next state; applying the RL action generator to the simulated next state to determine the next recommended treatment action for a patient; and determining whether the convergence in the RL action generator has been reached. The method further includes determining that the RL action generator has been optimized in response to determining that the convergence has been reached, receiving a patient state as a query, applying the optimized RL action generator to the received patient state to determine an optimized recommended treatment action for the received patient state, and outputting the optimized recommended treatment action for the received patient state.

In aspects of the present disclosure, apparatus, systems, and computer program products in accordance with the above aspect may also be provided. Any of the above aspects may be combined without departing from the scope of the present disclosure.

BRIEF DESCRIPTION OF THE DRAWINGS

The details of the present disclosure, both as to its structure and operation, can be understood by referring to the accompanying drawings, in which like reference numbers and designations refer to like elements.

DETAILED DESCRIPTION

Figure 1:
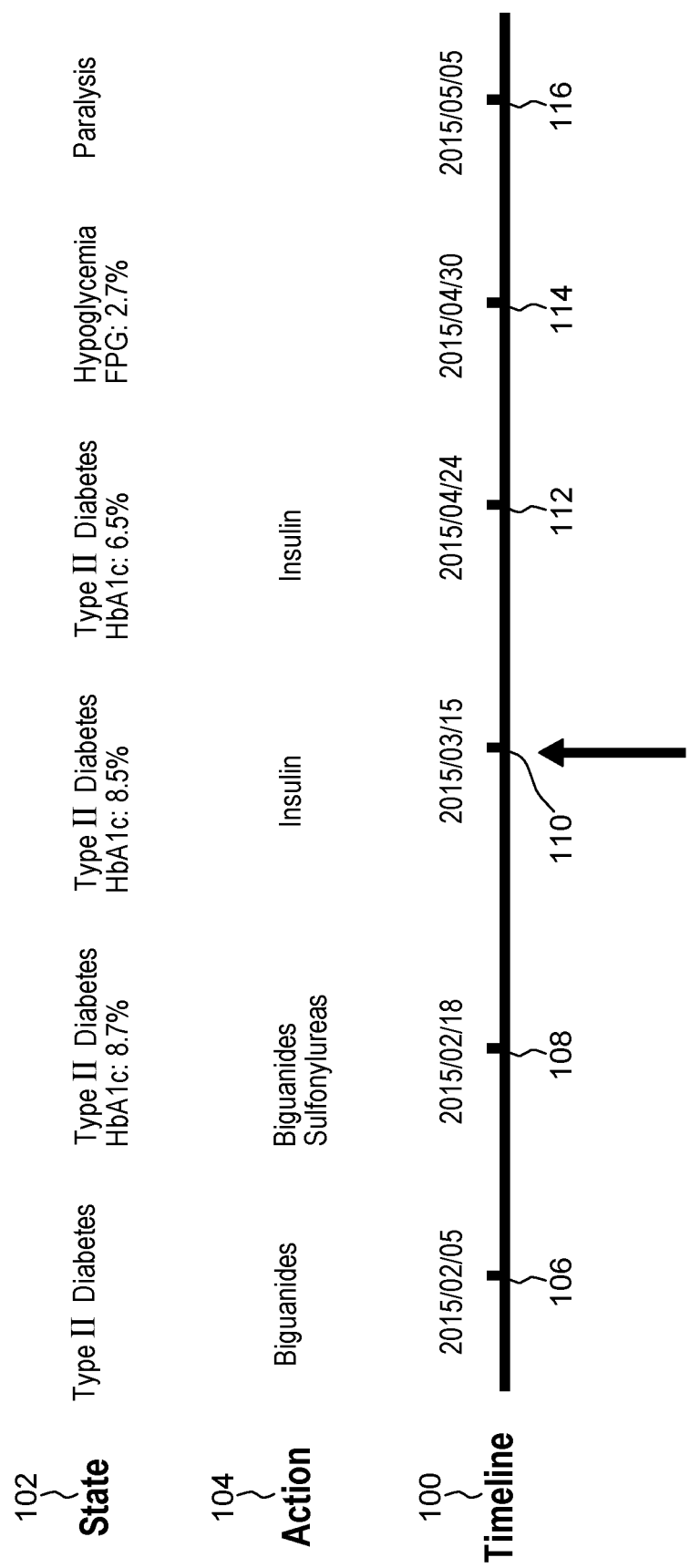
FIG. 1 is a diagram illustrating a patient treatment timeline including state and action information in accordance with some aspects of the present disclosure.

In aspects of the present disclosure, there is provided a system, method and computer program product for treatment recommendation. The system and method for treatment recommendation implements at a computing system Reinforcement Learning (RL) optimization with Recurrent Neural Network (RNN)-based simulation. By an RNN-based simulation, RL optimization gradually reaches an optimal treatment policy by reaching a convergence. Previous sequential patient observations may also be leveraged to provide a treatment recommendation and the long-term utilities for an optimal treatment recommendation may also be taken into account. The combination of RL optimization with a RNN-based simulation framework allows for the simulation of future states and actions to estimate the future effects of state based actions on the long-term goals, e.g., future states, of a patient's treatment plan.

As an example, the long-term goal of diabetic patients is to avoid complication diseases such as stroke and heart failure, while the short-term goal is to well control the blood glucose such as HbA1c <7.0%. Often the recommended treatment for long-term and short-term goals may be different. For example, a recommended treatment for the short-term goal of controlling blood glucose may involve the use of insulin shots while the recommended treatment for a long-term goal such as preventing stroke or heart failure may include additional or alternative treatments. For example, oral hypoglycemic drugs may be an alternative treatment to insulin. Generally, oral hypoglycemic drugs will not suddenly drop off the blood glucose, so as to avoid hypoglycemia incidents. Additional example treatments may include a combination of treatments for controlling blood glucose, blood pressure, blood lipid and anti platelet. For example, the short-term goal is still controlling blood glucose, since the patient is diabetic, and the long-term goal is a comprehensive chronic disease management.

In some cases, the recommended treatment for a long-term goal may overlap with the recommended treatment for a short-term goal, e.g., the patient may receive both treatments. In some cases, the recommended treatment for a long-term goal may conflict with the recommended treatment for a short-term goal. For example, the medications for the short and long-term goals, when taken together, may have an interaction that limits or inhibits one or both medications from performing as intended. As another example, the short term medication may inhibit the long term goal. For example, the short term utility for a patient with diabetes is to control blood glucose levels while the long term utility is to reduce the incidence and seriousness of diabetes complications. Insulin may be used to provide the short term benefit (e.g., maintaining HbA1c value below 7) but from a long-term perspective, too much lowering of blood glucose may result in hypoglycemia or even paralysis. Because of this, the long term utility should be considered when determining the treatment action for a short term goal and the long and short term goals need to be weighed and balanced. For example, by learning from historical treatment and outcome data, balanced patterns between actions directed toward short term goals and their corresponding long term effects may be determined.

With reference to FIG. 1, an example timeline 100 of the progression of a disease, e.g., Type II Diabetes, over time is charted. A state timeline 102 of the patient's state and an action timeline 104 that is taken for each state is shown recorded. For example, at a date 106 on timeline 100, a patient with a state 102 of Type II Diabetes may be given Biguanides as an action 104. At a date 108 on timeline 100, the patient's state 102 has changed to Type II Diabetes with an HbA1c of 8.7% and the patient is given both Biguanides and Sulfonylureas as an action 104. At a date 110 on timeline 100, the patient's state 102 has changed to Type II Diabetes with an HbA1c of 8.5% and the patient is given Insulin as an action 104. At a date 112 on timeline 100, the patient's state 102 has changed to Type II Diabetes with an HbA1c of 6.5% and the patient given Insulin as an action 104. At a date 114 on timeline 100, the patient's state 102 has changed to Hypoglycemia with a FPG of 2.7%. No action is shown as taken at 114. At a date 116 on timeline 100, the patient's state 102 has changed to paralysis. No action is shown as taken at 116. While described with reference to dates, any other period of time may be used including hours, minutes, or other measures of time.

At any given point in timeline 100, a treatment recommendation may be determined. In some aspects, the treatment recommendations may be determined based on the patient's current state, prior states, a rate of change of states, e.g., how fast the patient's state is deteriorating, previous actions taken, or other similar criteria. As an example, at date 110, treatment recommendations may be determined not only based on the patients state 102 of Type II Diabetes with an HbA1c of 8.5%, but also based on prior treatment actions, e.g., the administration of Biguandides and Sulfonylureas at date 108, and prior states, e.g., no HbA1c warning at date 106 and a HbA1c of 8.7% at date 108.

In some aspects, the state, date, and action timelines are generated from data provided by a caregiver, e.g., a medical doctor, by a medical records system, or any other source of medical information, and may be stored in a database associated with a computer system.

Figure 2:
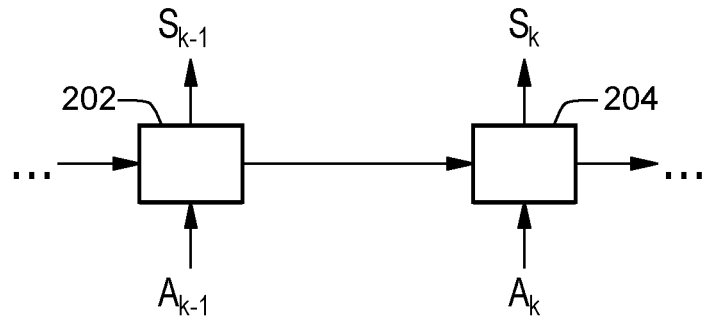
FIG. 2 is a diagram showing a portion of a Recurrent Neural Network (RNN) simulator in accordance with some aspects of the present disclosure.

With reference now to FIG. 2, a recurrent neural network (RNN) may be used to simulate treatments by analyzing a combinations of states, e.g., $S_k$, $S_{k-1}$, etc., and actions $A_k$, $A_{k-1}$, etc. from the timeline data. As known, an RNN may be a software or hardware construct of inter-connected nodes forming an artificial neural network wherein connections between nodes form a directed cycle. In some aspects, states may include data that captures or represents physical attributes such as, for example, age, weight, height, or other similar attributes, type of disease, e.g., Type II Diabetes, disease states, e.g., HbA1c levels, FPG levels of a patient or any other physiological state of a patient or level that may be used to determine a progression of a disease. In some aspects, for example, as illustrated in FIG. 2, the RNN node at each date on the timeline, illustrated as nodes 202 and 204, generates states, e.g., $S_k$, $S_{k-1}$, etc., based on a current action, e.g., actions $A_k$, $A_{k-1}$, etc.

An example RNN architecture that may be used is the long short-term memory (LSTM) architecture which allows data to flow both forward and backwards within the network. Other known RNN architectures may also be used.

While RNN based state determinations may be used to determine a state based on a current action and, in some aspects, a previous RNN state, an RNN, used alone, my not be suitable for determining an optimal treatment recommendation for a long-term future goal. For example, by only taking into account current and prior state or action information, the RNN may not take into account potential recommended treatment actions for future states of the patient, e.g., recommended treatment actions for two, three, four or more future states.

Figure 3:
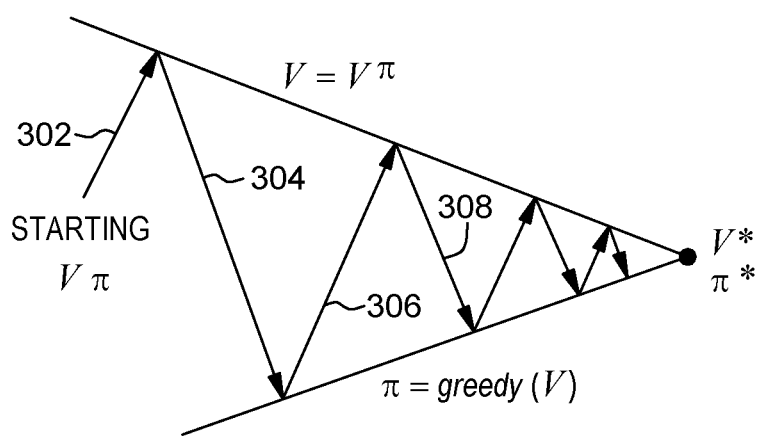
FIG. 3 is a diagram of a Reinforcement Learning (RL) technique in accordance with some aspects of the present disclosure.

With reference now to FIG. 3, reinforcement learning (RL) optimization may be used to perform optimization of treatment recommendations. The optimization occurs through iterative computation until a convergence is reached as illustrated by the arrowed lines 302, 304, 306, 308, etc. RL optimization typically requires that follow-up states be determined or simulated in advance to allow a convergence to be calculated. In the case of disease treatment, however, future patient states or determinations on whether or not a patient will take recommended actions cannot be easily simulated for use in standard RL optimization.

With continued reference to FIG. 3, V is the value of a state, π is the policy, V* is the optimal value and π* is the optimal policy. In the RL optimization, each state has a value, e.g., the state of HbA1c <=7.0% means the well-controlled blood glucose, and its value could be a positive value, while the state of HbA1c >7.0% might have a negative value. The RL optimization functions to compute the optimal policy π* so that for each state, the RL optimization function recommends an action that will result in a different state or a number of different states. In some aspects, for example, the recommended action may result in numerous potential states for which new actions may be determined. The RL optimization function may then recommend follow-up actions by π* again which may result in further follow-up states. In this way, π* is computed to make sure the total utility (by summing up the values of states) is optimal. Some known example approaches to RL optimization that may be used include value function approaches, Monte Carlo methods, temporal difference methods, direct policy search, brute force approaches, and criterion of optimality.

The total value V as computed by following the policy $\pi$ is denoted as $V^\pi$. Greedy(V) is one way to compute the optimal policy $\pi^*$, e.g., by using a greedy algorithm at each step. The greedy algorithm may provide more efficient optimization and usage of computer resources. For example, a greedy algorithm follows a problem solving heuristic of making the optimal choice at each stage with the hope of finding a global optimum. As the RL optimization iteratively computes $V^\pi$, the value of $V^\pi$ will converge to the optimal value $V^*$.

While RL optimization may be used to optimize the value V and the policies $\pi$ that are used to recommend actions for various states, RL optimization alone may not be fully capable of optimizing for future states due to the absence of a reliable simulation of future states for diseases. Thus, there is a need for a way to generate an RL optimization function that is trained to optimize treatment recommendations that take into account the impact of the treatment recommendations on potential future states for diseases.

Figure 4:
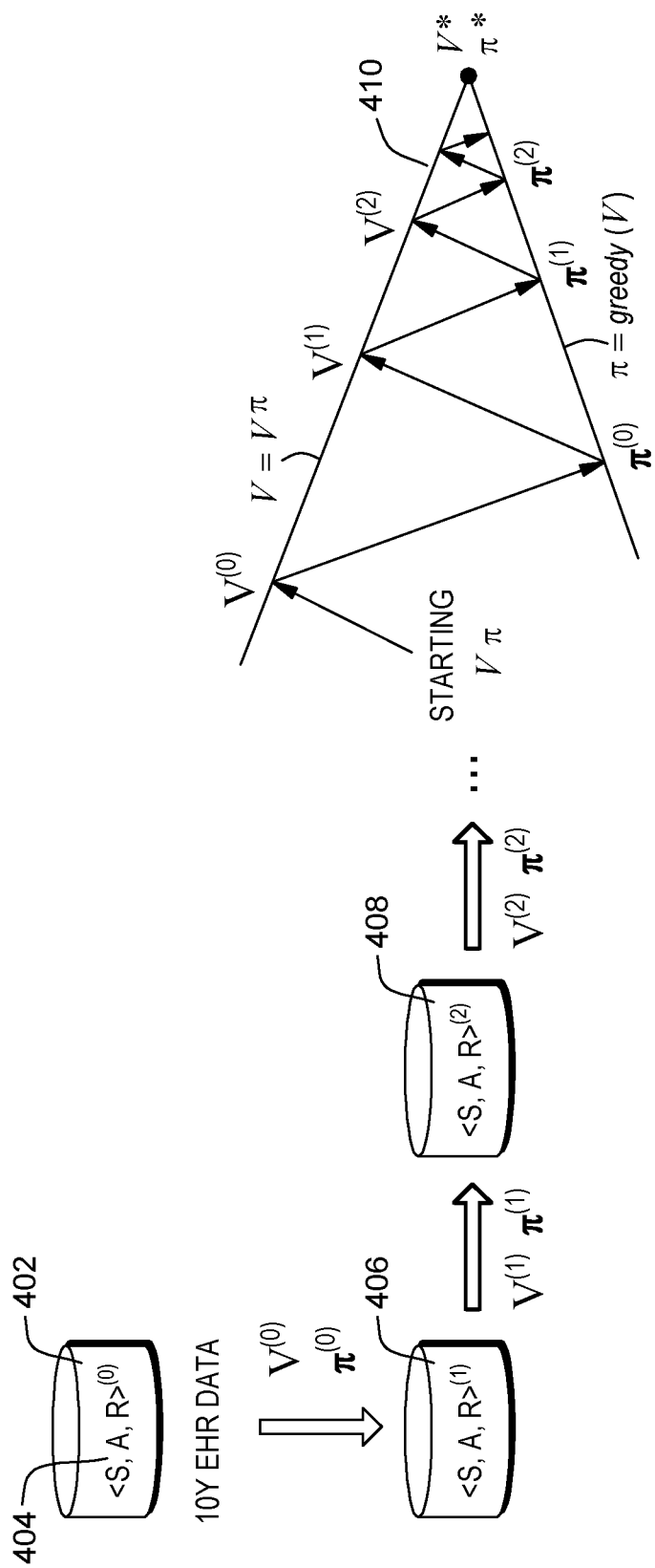
FIG. 4 is a block diagram illustrating an example optimization performed by the RL technique in accordance with some aspects of the present disclosure.
Figure 8:
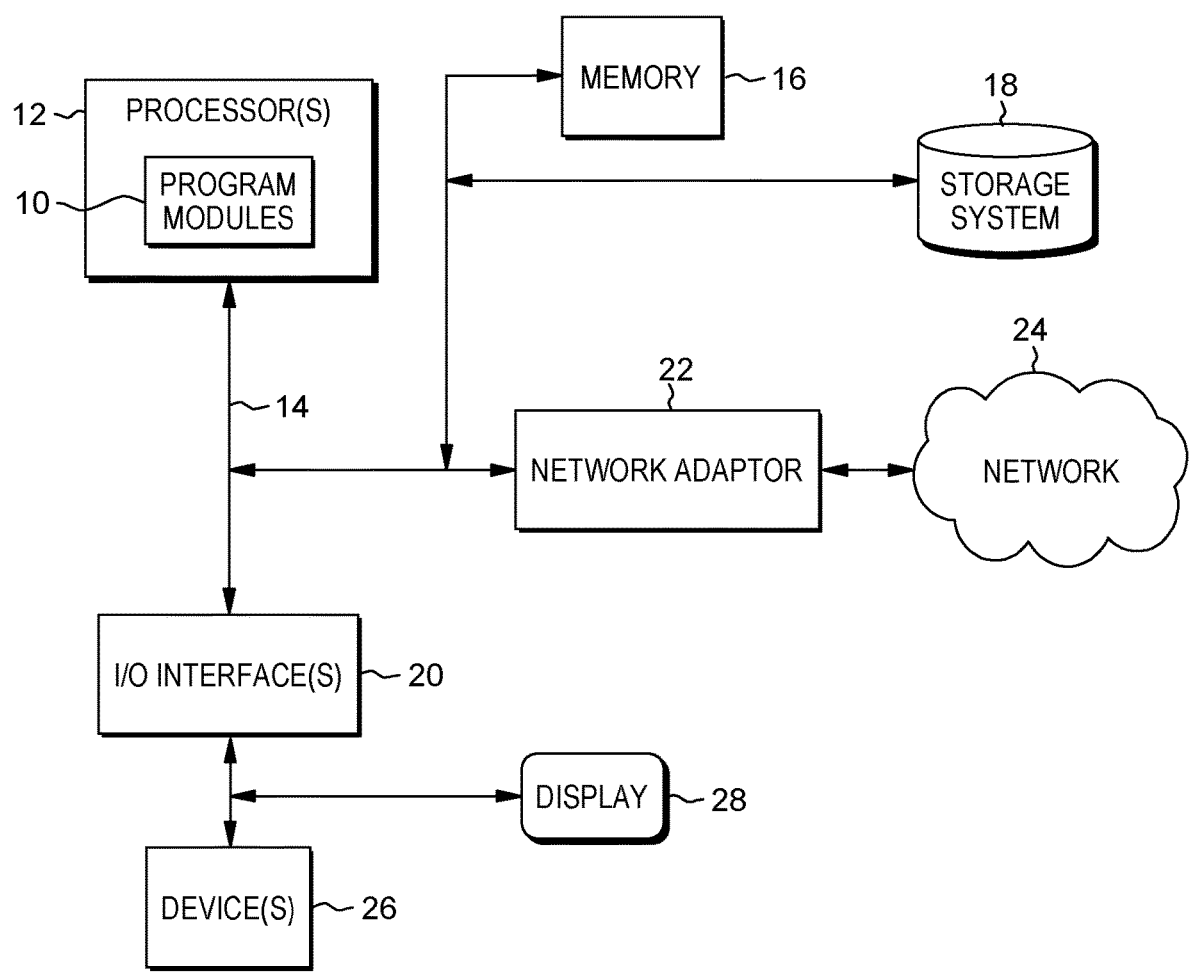
FIG. 8 is an exemplary block diagram of a computer system in which processes involved in the system, method, and computer program product described herein may be implemented.

With reference now to FIG. 4, an improvement to normal RL based policy optimization is illustrated. In FIG. 4, a database 402, e.g., a database associated with a computer system such as shown in FIG. 8, may store an electronic health record (EHR) or other patient data as a data vector 404, e.g., having state, action, reward (SAR) values. In some aspects, the EHR data for the SAR vector may, for example, be EHR data for a pre-defined period of time. For example, the EHR data for the SAR vector may be EHR data for a patient over a 10 year period of time.

In some aspects, a SAR vector may be defined by the following equations:

$$V_\pi(s) = \sum_{a \in A} \pi(a|s) q_\pi(s, a) \quad (1)$$

$$q_\pi(s, a) = R_s^a \gamma \sum_{s'} \square \in S + P_{ss'}^a v_\pi(s') \quad (2)$$

$$v_a(s) \max_{aq_\pi(s,a)} \square \quad (3)$$

Where:
$V_\pi$ is the total value.
s is the state.
a is an action.
A is the set of actions.
$q_\pi(s,a)$ is the expected return value, starting from state s, taking action a, and then following policy $\pi$.
$R_s^a$ is the expected return value under state s when taking action a
$\gamma$ is the discounted factor
$P_{ss'}$ is the transition probability from s to s', following a.
S is the set of states.
s' is the follow-up state after applying the action a on the state s.
$v_*(s)$ is the optimal return value, staring from state s (only the action making $q_*(s,a)$ maximum will be taken, so it's unnecessary to input any action a)
$q_*(s,a)$ is the optimal return value, staring from state s, taking action a.

In some aspects, for example, an initial SAR vector 404, e.g., $<S,A,R>^{(0)}$, may be determined based on equations (1)-(3) and the results $V^{(0)}$ and $\pi^{(0)}$ after applying RL optimization may be applied to equations (1)-(3) for a subsequent SAR vector 406, e.g., $<S, A, R>^{(1)}$. The results $V^{(1)}$ and $\pi^{(1)}$ of SAR vector 406 after applying RL optimization may then be applied to equations (1)-(3) for a subsequent SAR vector 408, e.g., $<S, A, R>^{(2)}$, and so on. Vector diagram 410 shows the progression of the value V that converges toward the optimum value $V^*$ via results $V^{(0)}$, $V^{(1)}$, $V^{(2)}$ and etc., the policy $\pi$ to the optimum policy $\pi^*$ according to policies $\pi^{(0)}$, $\pi^{(1)}$, $\pi^{(2)}$ and etc., using RL optimization.

Figure 5:
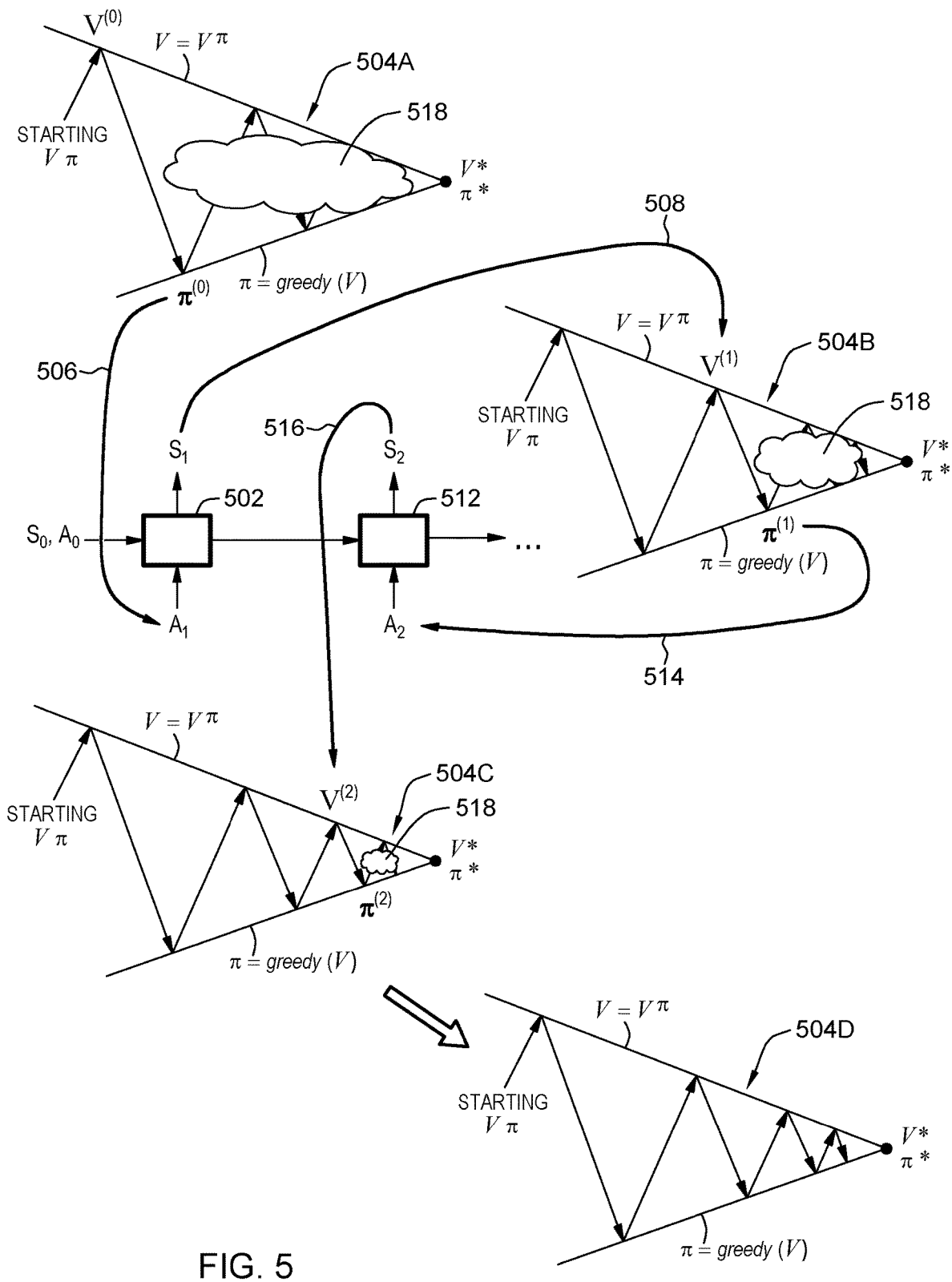
FIG. 5 is a diagram illustrating a combined RNN and RL technique for simulating future states and actions in accordance with some aspects of the present disclosure.

With reference now to FIG. 5, training a RL optimization function using RNN state simulation is disclosed. Given an initial state $S_0$, an initial action $A_0$, and a recommended action $A_{(1)}$, a RNN node 502 may simulate a state $S_1$. For example, the initial state $S_0$ and initial action $A_0$ may be received from patient database 402. The recommended action $A_{(1)}$ may be determined based on RL optimization of an initial value $V^{(0)}$ and policy $\pi^{(0)}$, e.g., based on the historical EHR data stored in database 402 or based on the initial state $S_0$, using a RL optimization 504A and received by the RNN node 502 at 506. Recommended action $A_1$ is fed as an input to a RNN node 502, and state $S_1$ is generated according to the prediction of the RNN node 502. State $S_1$ triggers a further RL optimization 504B at 508 to perform RL optimization using the next value $V^{(1)}$ and based on a policy $\pi^{(1)}$ to generate a recommended action $A_2$. Recommended action $A_2$ is fed as an input to a RNN node 512 at 514, and state $S_2$ is generated according to the prediction of the RNN node 512 based on the recommended action $A_2$. In some aspects, numerous potential states $S_2$ may be predicted by RNN node 512. State $S_2$ triggers RL optimization 504C to optimize the next value $V^{(2)}$ and based on a policy $\pi^{(2)}$ at 516. In some aspects, if numerous potential states S2 are predicted, each state S2 may trigger a RL optimization 504C. This process of iterative optimizations using both RNN state prediction and RL optimization to generate recommended actions continues until the optimum value $V^*$ according to an optimum policy $\pi^*$, e.g., a convergence, has been reached. For example, a convergence may be reached when there are no changes or minimal changes below a pre-determined threshold amount in the value V and policy $\pi$ for a certain number of iterations or a finite period of time. For example, a delta of $V_{now} - V_{pre}$ may be determined where $V_{now}$ is the value of the current result and $V_{pre}$ is the value of the previous result. If the Delta is less than a pre-determined threshold, e.g., 0.01, a convergence in the value V may be considered to have been convergence. A similar determination may be made for the policy $\pi$. In some aspects, for example, once convergence for V and $\pi$ is reached, the optimization process may be terminated. As illustrated in FIG. 5, for example, the masking cloud 518 found in the RL optimizations 504A-504C is reduced with each iteration until the computational convergence of value V and policy $\pi$ to the optimum value $V^*$ and optimum policy $\pi^*$ is reached in RL optimization 504D, e.g., masking cloud 518 is no longer present.

In some aspects, once the computational convergence of the RL optimization function has been reached, the training of the RL optimization function may be terminated and the RL optimization function may be used to recommend optimal treatments actions for the patient that take into account long term goals or outcomes based any state of the patient. In some aspects, for example, the recommended treatment actions for a patient may align with the recommended actions output from the RL optimization function where a future state is desired to achieve a long-term goal. In some aspects, for example, the patient may be provided with treatments based on the optimum recommended treatment actions and resulting simulated states where, for example, a future simulated state aligns with a long-term goal of the patient's care. In some aspects, RL optimization function may continue to be trained as new patient state, action, or other timeline data is received. For example, changes in a patient's state in response to a recommended treatment action may be used to further train the RL optimization function and new future states may also be simulated by the RNN for further training.

Figure 6:
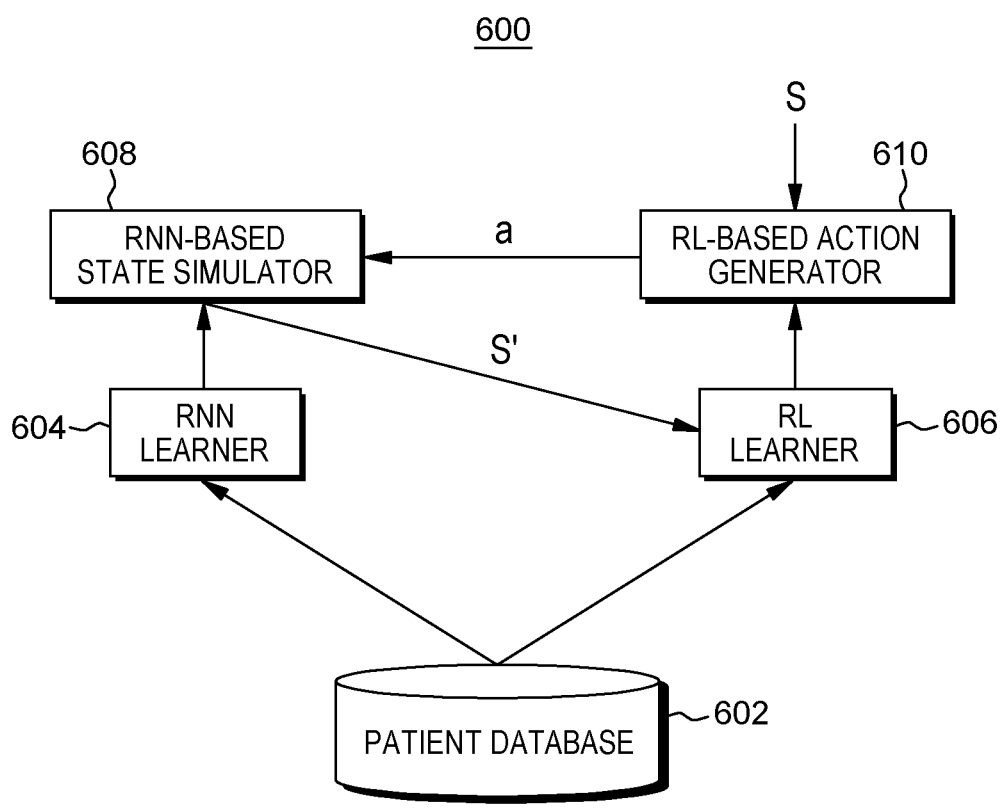
FIG. 6 is a system diagram of a system for implementing the combined RNN and RL technique of FIG. 5 in accordance with some aspects of the present disclosure.

With reference now to FIG. 6, a computer-implemented system 600 for RNN-based reinforcement learning for treatment recommendation is disclosed. In some aspects, system 600 includes a patient database 602, an RNN learner 604, a RL learner 606, a RNN-based state simulator 608, and a RL-based action generator 610.

Patient database 602 store patient data including, for example, historical states, historical actions performed, historical follow-up states that occurred based on the historical actions performed, timelines, physical attributes, or any other information related to the patient, disease, diagnoses, treatments, and outcomes. For example, the state, action, and timeline data illustrated in FIG. 1 may be stored in patient database 602 as patient data. As an example, patient database 602 may include database 402 and store data vectors such as SAR vectors 404-408.

RNN learner 604 is a training model for training the RNN-based state simulator 608. For example, RNN learner 604 may generate learning data for RNN-based state simulator 608 from the patient data stored in patient database 602. In some aspects, for example, RNN learner may be a sequential data learning model. In some aspects, for example, historical state and historical action information for a patient may be fed into RNN learner 604 and RNN-based state simulator 608 may be trained to simulate outcome states based on the historical state and action information. For example, a first historical state and a first historical action and an expected second state, e.g., a historical state occurring as a result of the first historical action, may be input into RNN learner 604 and used to train the RNN-based state simulator 608 to simulate the expected second state from the first state and action. In some aspects, the input historical state and action information may be included as part of the EHR data in patient database 602.

RL learner 606 is a training model for training the RL-based action generator 610. For example, RL learner 606 may use a Q-learning reinforcement learning technique based on the patient data stored in database 602 and follow-up simulated state information S' received from RNN-based state simulator 608. For example, in the Q-learning technique, an agent can perform an action to move from state to state. When the agent executes an action in a specific state, the agent receives a reward (e.g., a numerical score). The goal of the agent is to maximize its total received reward. For example, the agent may maximize the total received reward by learning which action is optimal for each state, e.g., based on the patient data. As an example, the action that is optimal for each state may be the action that has the highest long-term reward where the long term reward may be a weighted sum of the expected values of the rewards of all future steps starting from the current state. The weight for a step from a state $\Delta t$ steps into the future may be calculated as $\gamma^{\Delta t}$ with $\gamma$ being a number between 0 and 1 ($0 \le \gamma \le 1$) called the discount factor that trades off the importance of sooner versus later rewards. $\gamma$ may also be interpreted as indicating the likelihood to succeed (or survive) at every step $\Delta t$.

As illustrated in FIG. 6, the RNN-based simulator 608 learns from RNN leaner 604 and supplies as an output the follow-up simulated state information S' to RL learner 606. RL learner 606 trains RL-based action generator 610 using patient data from patient database 602 and the follow-up simulated state information S' from RNN-based state simulator 608. RL-based action generator 610 outputs recommended treatment actions a to the RNN-based state simulator 608 during training which are then used by RNN-based state simulator 608 to generate further follow-up simulated state information S' for input to RL learner 606. Once optimization is reached during training of RL-based action generator 610, as described above, RL-based action generator 610 may be considered trained and ready for use in generating optimal treatment recommendations.

Once trained, the RL-based action generator 610 generates new recommended actions a based on the training from RL learner 606 and a received state S, e.g., a state provided as a query to the RL-based action generator 610. For example, the query may include a request for an optimal recommended treatment action given a state S of a patient, e.g., a current state or a state from a specific date in the patient data stored in patient database 602.

As further illustrated in FIG. 6, once a recommended action a has been generated by RL-based action generator, the recommended action a may be fed back into the RNN-based state simulator 608 for further generation of simulated follow-up states S' that may then be fed back into RL learner 606 to further train the RL-based action generator through RL optimization as described above.

Figure 7:
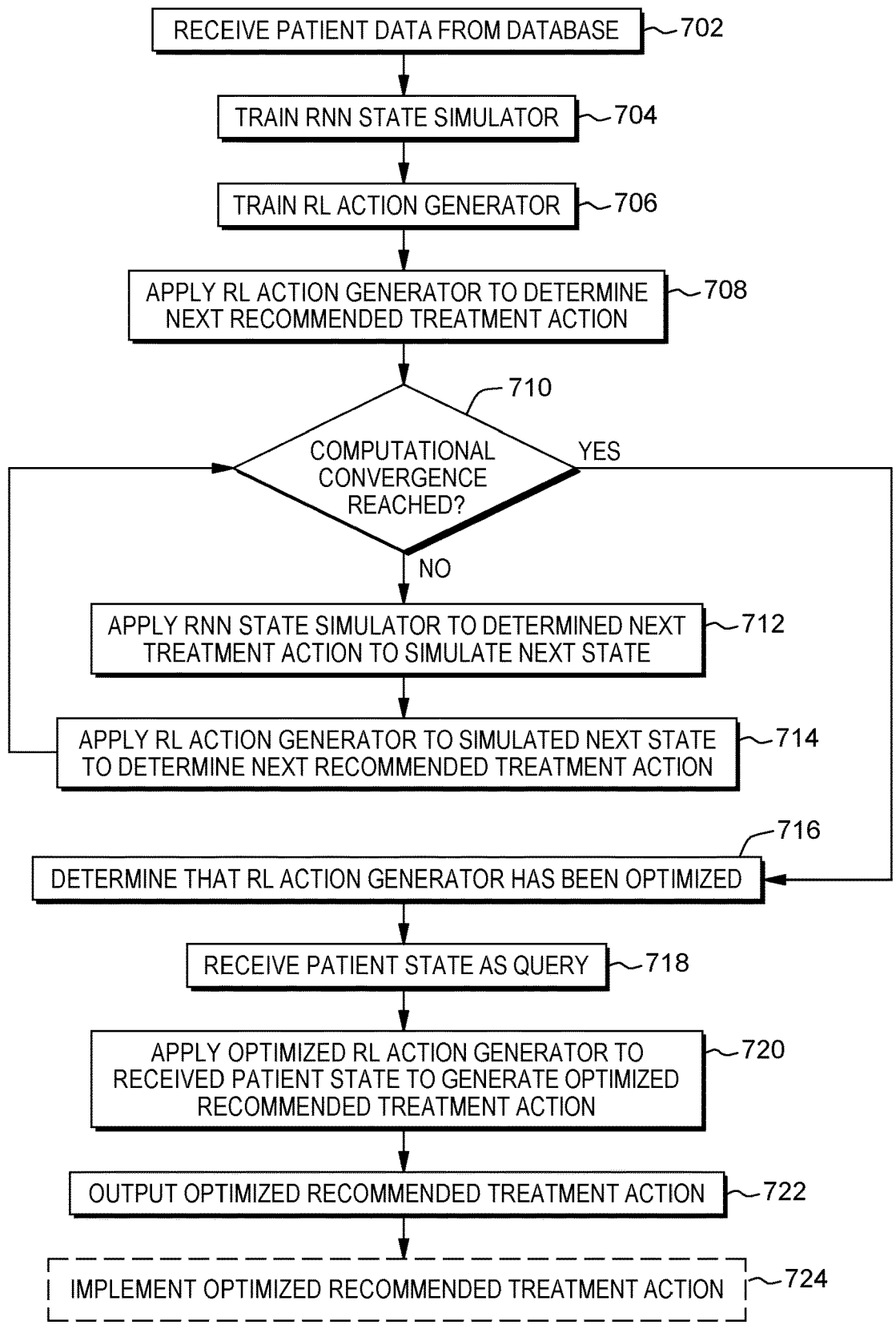
FIG. 7 is a flow chart of a method for simulating future states and actions to determine recommended treatments in accordance with some aspects of the present disclosure.

With reference now to FIG. 7, a method 700 for generating an optimized recommended treatment action is illustrated.

At 702, patient data of a patient is received from patient database 602.

At 704, the RNN state simulator 608 is trained, e.g., by RNN learner 604 as described above.

At 706, the RL action generator 610 is trained, e.g., by RL learner 606 as described above.

At 708, the RL action generator is applied to a state of a patient in the patient data to determine a next recommended treatment action for the patient. For example, the state may be received as an input to the RL learner 606, e.g., from patient database 602 or RNN state simulator 608 and RL action generator 610 may determine a next recommended treatment action based on the state and the training of the RL action generator 610 described above.

At 710, a determination of whether a computational convergence has been reached for the RL action generator 610.

If the computational convergence is has not been reached, the RL action generator 610 may be optimized by applying the RNN state simulator to the determined next treatment action at 712 to simulate a next state, applying the RL action generator to the simulated next state to determine a next recommended treatment action at 714. The method then returns to 710 to once again determine whether the computational convergence for the RL action generator 610 has been reached and steps 712 and 714 are repeated if no convergence is determined to be reached. This optimization using simulated future states allows the RL action generator to be optimized for generating recommended actions that take into account potential future states as a way of taking into account long term goals in treatment recommendations.

If the computational convergence is determined to be reached, the method proceeds to 716 the RL action generator 610 is determined to have been optimized.

At 718, a patient state is received as a query, e.g., a state of an actual patient, a state selected from the patient database 602, or a patient state received in any other way. In some aspects, for example, a clinician may input a current patient state for an actual patient suffering from a disease.

At 720, the optimized RL action generator is applied to the received patient state to generate an optimized recommended treatment action that takes into account long-term goals of the patient.

At 722, the optimized recommended treatment action is output. For example, the optimized recommended treatment action may be presented via a display of a computing device to a clinician or other medical personnel in charge of treating a patient.

At 724, in some aspects, the method may implement the optimized recommended treatment action, e.g., by providing the recommended treatment to the patient or causing the recommended treatment to be provided to the patient.

FIG. 8 illustrates a schematic of an example computer or processing system that may implement any portion of system 100, computing device 110, consumer computing device 130, systems, methods, and computer program products described herein in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a software module 10 that performs the methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method implemented by at least one processor comprising hardware, the method comprising:
   receiving patient data of a plurality of patients from a patient database;
   training a Reinforcement Learning (RL) action generator based at least in part on the received patient data of a plurality of patients to generate recommended treatment actions based on at least one state of a patient;
   training a Recurrent Neural Network (RNN) state simulator based at least in part on the patient data of the plurality of patients to simulate new states of a patient based on recommended treatment actions generated by the RL action generator;
   applying the RL action generator to a state of a patient in the received patient data to determine a next recommended treatment action for the patient;
   determining whether a convergence in the RL action generator has been reached;
   optimizing the RL action generator until the convergence in the RL action generator is determined to be reached by iteratively repeating:

applying the RNN state simulator to the determined next recommended treatment action to simulate a next state;

applying the RL action generator to the simulated next state to determine the next recommended treatment action for a patient, the applying the RNN state simulator comprising: at an iteration, receiving, as inputs to a simulator node of said RNN, a prior simulated state from an immediate prior simulator iteration, an immediate prior treatment action for the patient, and the determined next recommended treatment action from said RL action generator to generate the next simulated state;

determining whether the convergence in the RL action generator has been reached;

determining that the RL action generator has been optimized in response to determining that the convergence has been reached; and receiving a patient state as a query;

applying the optimized RL action generator to the received patient state to determine an optimized recommended treatment action for the received patient state; and outputting the optimized recommended treatment action for the received patient state.

2. The method of claim 1, wherein the computational convergence is a convergence of an expected return value of a treatment action recommended by the RL action generator, and a convergence of a policy used to recommend the next treatment action based on a simulated state.

3. The method of claim 2, wherein the policy of the RL action generator implements a greedy policy to determine the next recommended treatment action for the patient.

4. The method of claim 1, further comprising providing a treatment recommendation to a patient based on the optimized recommended treatment action.

5. The method of claim 1, wherein the RL action generator is trained based at least in part on a state simulated by the RNN state simulator.

6. The method of claim 1, wherein the patient data comprises historical information about the plurality of patients, the historical information comprising historical states of the plurality of patients, historical treatment actions taken in response to the historical states, and new historical states of the plurality of patients that occurred as a result of the historical treatment actions.

7. The method of claim 1, wherein said determined next recommended treatment action from said RL action generator is a single treatment action optimized without observing future patient states.

8. The method of claim 7, further comprising:

running, at said RL action generator, an optimization function for determining each said next single recommended treatment action and successive next single recommended treatment actions at corresponding successive iterations, each determined next and successive recommended treatment action based on generating a corresponding next expected value and a corresponding next policy successively determined based on a corresponding current generated next simulated state from said RNN simulator node, said optimization function computing an optimal policy responsive to each generated next simulated state.

9. The method of claim 8, wherein, at each iteration, the optimization function is configured by said at least one processor to recommend a next single treatment action that will result in a plurality of different next simulated states, wherein said iteratively repeating further comprises:

responsive to each plurality of different next simulated states, triggering a next successive optimization using a expected return value and a policy to generate the next single recommended treatment action, and using each next single recommended treatment action as an input to a next connected RNN simulator node of a sequence of RNN generator nodes to generate a next simulated state according to a prediction of the RNN node based on the received next single recommended treatment action.

10. The method of claim 8, further comprising:

storing data vectors in an associated memory storage device, a data vector having a simulated state, a recommended action, and an expected reward value, said optimization function updating a data vector for use at each iteration such that said expected return value and a corresponding optimal policy reach said convergence.

11. The method of claim 7, further comprising: configuring said RNN state simulator as a long short-term memory (LSTM) recurrent neural network structure.

* * * * *